acid addition salt forms in conventional manner, and vice versa.

Representative acids for acid addition salt formation include the organic acids such as tartaric acid, fumaric acid, oxalic acid, and maleic acid and the mineral acids such as the hydrohalide acids.

The compounds of formula I have not been described in the literature.

The compounds of formula I are useful because they possess pharmacological activity in animals. In particular, the compounds of formula I are useful as agents for the treatment of cerebral insufficiency in animals as indicated by an increase in vigilance indicated in the following standard tests in animals, by:

i. A prolongation of the waking phase, a shortening of the classical sleep phases, a shortening of the paradoxical sleep phases and a prolongation of the latency period till the onset of first paradoxical sleep, as determined by E.E.G. measurements in the non-narcotized rat on i.p. administration of from 3 to 10 mg per kilogram animal body weight, of the compounds.

ii. A reduction in the number of P.G.O. spikes in the "Corpus geniculatum laterale" induced by reserpine in cats on i.v. administration of from 0.1 to 0.5 mg per kilogram animal body weight, of the compounds, and iii. An antagonism of the E.E.G. changes relating to $\alpha$, $\beta$ and $\Delta$ waves induced by ischemia in the perfused cat head on administration of from 100–500 mg, of the compounds, wherein similar effects are obtained to the known ceberal insufficiency agent HYDERGIN (Registered Trade Mark).

For the above mentioned use the dosage will, of course, vary depending on the compound employed, mode of administration and therapy desired. However, in general, satisfactory results are obtained when administered at a daily dosage of from 0.1 mg to about 10 mg per kg animal body weight, conveniently given in divided doses 2 to 4 times a day or in sustained release form. For the larger mammal, the total daily dosage is in the range from about 5 to about 60 mg, and dosage forms suitable for oral administration comprise from about 1 mg to about 30 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acids for acid addition salt formation include organic acid salt forms such as the tartaric, fumaric, oxalic and maleic acids and methane sulphonate and mineral acids such as the hydrochloric, hydrobromic and sulphuric acids. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

In a preferred group of compounds $R_2$ is isobutyl (2-methylpropyl), or especially isopropyl (1-methylethyl) or benzyl.

In the following non-limitative Examples all temperatures are indicated in degrees Centigrade. Room temperature is from 15° to 30° C. A suitable vacuum is between 8 and 20 nm Mercury unless otherwise stated.

EXAMPLE 1

13-bromo-9,10-dihydro-ergotamine

A solution of 3.01 cc (35 millimols) of oxalyl chloride in 50 cc of absolute acetonitrile is added dropwise at −30° within 5 minutes, while stirring, to 70 cc of absolute dimethyl formamide and 140 cc of absolute acetonitrile, and the crystalline mash is stirred at −30° for a further 5 minutes. 12.25 g (35 millimols) of anhydrous 13-bromo-9,10-dihydrolysergic acid are subsequently added, the suspension is stirred at 0° for 30 minutes, is cooled to −30° and 24.5 cc of pyridine and 5.85 g (17.5 millimols) of (2R,5S,10aS,10bS)-2-methyl-2-amino-5-benzyl-3,6-dioxo-10b-hydroxy-octahydro-8H-oxazolo[3,2-a]pyrrolo[2,1-c]pyrazine hydrochloride are successively added. After stirring at 0° for 2 hours, the reaction mixture is poured onto ice, extracted with methylene chloride, and the methylene chloride phases are successively washed with a 10% soda solution and water, dried and concentrated by evaporation. The residue is crystallized from acetone/ether. The title compound is obtained in the form of colourless crystals having a M.P. of 248–250° (decomp.); $[\alpha]_D^{21} = -53°$ (c = 0.5; pyridine).

EXAMPLE 2

13-bromo-9,10-dihydro-ergotamine 1.58 cc (10.5 millimols) of trifluoroacetic acid anhydride are added at −20° within 10 minutes to a suspension of 3.5 g (10 millimols) of anhydrous 13-bromo-9,10-dihydro-lysergic acid in 100 cc of absolute acetonitrile, in the absence of moisture while a stream of nitrogen is passed through. After stirring at −20° for 30 minutes, 2.23 g of (2R, 5S, 10aS, 10bS)-2-methyl-2-amino-5-benzyl-3,6-dioxo-10b-hydroxy-octahydro-8H-oxazolo[3,2-a]pyrrolo[2,1-c]pyrazine hydrochloride, dissolved in 7 cc of trifluoroacetic acid, and 13.5 cc of pyridine are rapidly and successively added to the yellow solution. The reaction mixture is stirred at −20° for 1 hour, 13.5 cc of water are subsequently added, concentration is effected at 30°, the residue is taken up in methylene chloride, is washed with a 10% soda solution and water, dried and concentrated by evaporation. Crystallization from acetone/other yields the title compound as colourless crystals having a M.P. of 248–250° (decomp.); $[\alpha]_D^{21} = -53° \pm 2°$ (c = 0.5; pyridine).

SUBSTITUTED 3-(2-PYRIDINYL)-4(1H)-QUINOLINONE N-OXIDES

This is a division, of application Ser. No. 611,036 filed Sept. 8, 1975, now U.S. Pat. No. 4,007,193, issued Feb. 8, 1977.

DESCRIPTION OF THE PRIOR ART

Osborne et al., in J. Heterocyclic Chem. 1: 138–140 (1964), describe the preparation of 1-phenyl-2-(2-pyridinyl)ethanone N-oxide by the acylation of 2-picoline N-oxide, using sodium amide in liquid ammonia as the condensing agent. No pharmacological activity is reported for this or related compounds described by Osborne et al.

DESCRIPTION OF THE PARTICULAR EMBODIMENTS

This invention relates to substituted 3-(2-pyridinyl)-4(1H)-quinolinone N-oxides having the formula I:

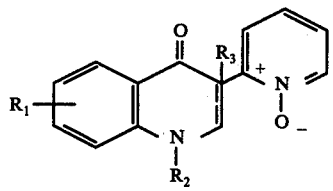

wherein $R_1$ is hydrogen, halogen, lower alkyl, hydroxy or alkoxy; $R_2$ is hydrogen or lower alkyl; $R_3$ is hydrogen or —$CH_2OH$; the dotted line indicates the possible presence of a double bond at the 2,3-position of the quinoline ring; and the pharmaceutically acceptable, acid addition salts thereof. Compounds of the formula I above wherein $R_1$ is hydrogen or halogen; $R_2$ is hydrogen or methyl; and $R_3$ is hydrogen or hydroxymethyl, as well as their pharmaceutically acceptable, acid addition salts, are particularly preferred.

The compounds of the invention having the formula II:

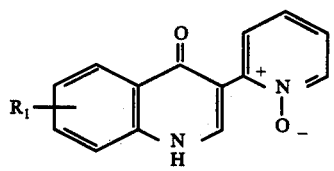

wherein $R_1$ is hydrogen, halogen, lower alkyl, hydroxy or alkoxy; are prepared by reacting a compound of the formula III:

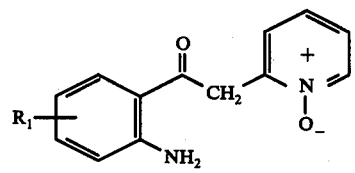

wherein $R_1$ is as defined above in compound II, with a trialkylorthoformate, typically triethylorthoformate. The reaction is conducted in a suitable solvent such as pyridine and the like, in the presence of an organic base, typically piperidine or pyrrolidine.

The compounds of the invention having the formula IV:

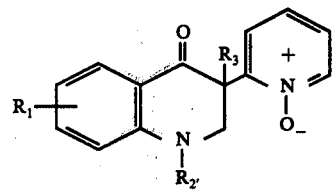

wherein $R_1$ is hydrogen, halogen, lower alkyl, hydroxy or alkoxy; $R_2'$ is lower alkyl; and $R_3$ is hydrogen or hydroxymethyl; are prepared by reacting a compound having the formula V:

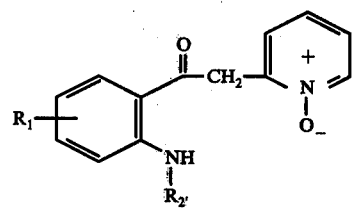

wherein $R_1$ and $R_2'$ are as defined above in compound IV, with either one or two moles of formaldehyde. If one mole of formaldehyde is used, one obtains a final product wherein $R_1$ and $R_2'$ are as defined above in compound IV, and $R_3$ is hydrogen. If two moles of formaldehyde are used, one obtains a final product wherein $R_1$ and $R_2'$ are as defined above in compound IV and $R_3$ is hydroxymethyl. The reaction is conducted in a suitable solvent, such as methanol and the like, in the presence of an organic base, typically piperidine or pyrrolidine.

The starting materials III and V used in preparing the compounds of this invention are prepared as described in co-pending U.S. Ser. No. 611,282, filed Sept. 8, 1975, now U.S. Pat. No. 4,056,619. Thus, compounds of the formula III and V are prepared by reacting an N-substituted isatoic anhydride having the formula VI:

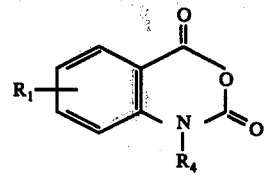

wherein $R_1$ is as defined above in compounds III and V and $R_4$ is hydrogen or lower alkyl, with a 2-picoline N-oxide of the formula VII:

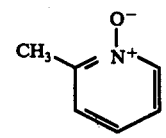

The above reaction is conducted in liquid ammonia in the presence of an alkali metal amide condensing agent ficed with ether, the dorsal skin reflected, and the mean orthogonal diameter of the reaction site measured.

A linear relationship can be shown to exist between the relative antibody concentration and the diameter of the resultant reaction if the antibody concentration is adjusted to yield diameters between approximately 7 ans 19 mm. For each experiment, a line is fitted by the least squares method for the relationship of the diameter to the relative antibody concentration to derive the base-line diameter. The percentage inhibition due to drug treatment is then calculated by the formula:

$$\% \text{ inhibition} = \left[1 - \frac{(\text{diameter of experimental} - \text{base value})}{(\text{diameter of control} - \text{base value})}\right] \times 100$$

The signficance of the inhibition is measured by Student's t-test.

For administration, the compounds are suspended by trituration in 1% gum tragacanth and 0.15M saline so as to give 10 ml/kg body weight.

Thus, the compounds of this invention are active for the inhibition of reagin-mediated allergic disorders when administered to mammals in need thereof at dose levels of from about 10 to about 25 mg/kg of body weight, by the oral or parenteral route. This dosage may be varied depending upon the severity of the condition, the age, weight, sex and class of mammal being treated, as well as the route of administration. For example, 2,3-dihydro-3-(hydroxymethyl)-1-methyl-3-(2-pyridinyl)-4(1H)-quinolinone N-oxide (the compound of Example 2) shows a 54% inhibition of the allergic response at 25 mg/kg when tested in a passive cutaneous anaphalaxis (PCA) screen, as described above. Consequently, the compounds of this invention are potentially useful in the treatment of asthma, hay fever and other allergic conditions.

In use, the compound of the invention may be combined with parenterally acceptable vehicles, such as gum tragacanth, in saline suspension, to provide dosage forms suitable for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

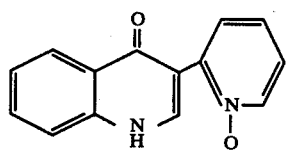

3-(2-Pyridinyl)-4(1H)-Quinolinone N-oxide

A solution of 1-[2-aminophenyl]-2-(2-pyridinyl)ethanone N-oxide (2.0 g), triethyl orthoformate (2.5 ml), pyridine (20 ml) and piperidine (15 drops) is refluxed under nitrogen for 20 hours. The product precipitates out. Recrystallization from N,N-dimethylformamide gives white crystals (0.9 g, 43%), m.p. dec 300° C.

Mass Spectrum observed molecular ion: 238.0788: calculated for $C_{14}H_{10}N_2O_2$: 238.0742.

EXAMPLE 2

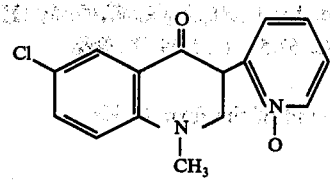

6-Chloro-2,3-Dihydro-1-Methyl-3-(2-Pyridinyl)-4(1H)-Quinolinone N-Oxide

A solution of 1-[5-chloro-2-(methylamino)phenyl]-2-(2-pyridinyl)ethanone N-oxide (15 g), 36% formaldehyde (0.9 m, 4.1 g), methanol (200 ml) and pyrrolidine (2 ml) is refluxed under nitrogen for 20 minutes. The solvents are removed under reduced pressure. Crystallized from isopropanol. Recrystallization from absolute ethanol gives bright yellow-green crystals (7.75 g, 49.5%), m.p. 135°–37° C.

Anal. Calcd. for $C_{15}H_{13}ClN_2O_2$: C, 62.40; H, 4.54; N, 9.70; Cl, 12.28. Found: C, 62.28; H, 4.62; N, 9.67; Cl, 12.19.

EXAMPLE 3

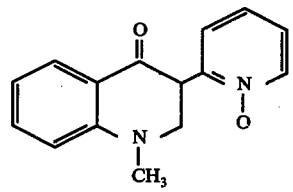

2,3-Dihydro-1-Methyl-3-(2-Pyridinyl)-4(1H)-Quinolinone N-Oxide

A solution of 1-[2-(methylamino)phenyl]-2-(2-pyridinyl)ethanone N-oxide (16.0 g), 36% formaldehyde (0.9 m, 4.96 g), methanol (100 ml) and pyrrolidine (4 ml) is refluxed under nitrogen for 50 minutes. The solvents are removed under reduced pressure. Crystallization from isopropanol gives yellow-green crystals (10.45 g, 62.2%), m.p. 132°–34° C.

Anal. Calcd. for $C_{15}H_{14}N_2O_2$: C, 70.85; H, 5.55; N, 11.02. Found: C, 70.67; H, 5.63; N, 11.02.

EXAMPLE 4

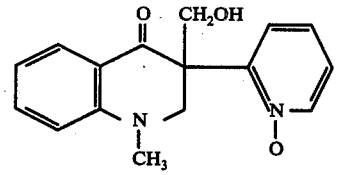

2,3-Dihydro-3-(Hydroxymethyl)-1-Methyl-3-(2-Pyridinyl)-4(1H)-Quinolinone N-Oxide.

A solution of 1-[2-(methylamino)phenyl]-2-(2-pyridinyl)ethanone N-oxide (15.0 g), 36% formaldehyde (41.0 g), methanol (150 ml) and pyrrolidine (2 ml) is refluxed under nitrogen for 30 hours. The product crystallized on cooling. Recrystallization from absolute ethanol gives greenyellow crystals (8.5 g, 50%), m.p. 198°–200° C.

Anal. Calcd. for $C_{16}H_{16}N_2O_3$: C, 67.59; H, 5.67; N, 9.85. Found: C, 67.58; H, 5.69; N, 9.84.

We claim:

1. A compound of the formula II:

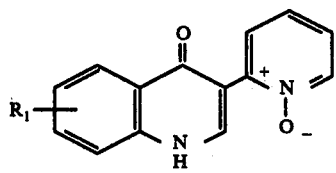

II wherein $R_1$ is hydrogen, halogen, lower-alkyl of 1 to 7 carbon atoms, hydroxy or alkoxy of 1 to 7 carbon atoms; and the pharmaceutically acceptable acid addition salts thereof.

2. A compound of the formula II according to claim 1 wherein $R_1$ is hydrogen or halogen.

3. A compound according to claim 1 which is 3-(2-pyridinyl)-4(1H)-quinolinone N-oxide.

4. A process for preparing a compound having the formula II:

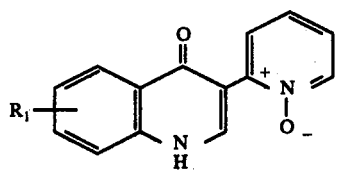

II wherein $R_1$ is hydrogen, halogen, lower alkyl of 1 to 7 carbon atoms, hydroxy or lower alkoxy of 1 to 7 carbon atoms, which comprises the step of reacting a compound of the formula III:

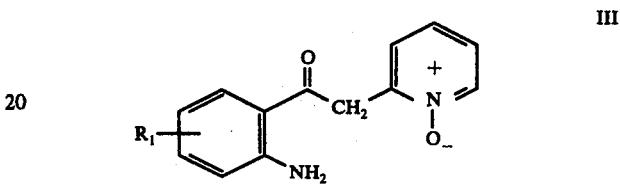

III wherein $R_1$ is as defined above in compound II with a trialkyl orthoformate to effect ring closure.

* * * * *